United States Patent [19]

Kiske et al.

[11] Patent Number: 4,922,900
[45] Date of Patent: May 8, 1990

[54] PUMPING ARRANGEMENT FOR SUPPLYING A VENTILATING APPARATUS WITH BREATHING GAS

[75] Inventors: Siegfried Kiske, Grönau; Thorsten Haase, Mölln; Thomas Leyer; Wolfgang Sauer, both of Lübeck, all of Fed. Rep. of Germany

[73] Assignee: Drägerwerk Aktiengesellschaft, Lübeck, Fed. Rep. of Germany

[21] Appl. No.: 352,360

[22] Filed: May 16, 1989

[30] Foreign Application Priority Data

May 19, 1988 [DE] Fed. Rep. of Germany ....... 3817092

[51] Int. Cl.$^5$ .............................................. A62B 9/04
[52] U.S. Cl. ............................... 128/202.27; 417/472; 417/360
[58] Field of Search .................. 128/202.27; 417/360, 417/472, 449, 450, 238

[56] References Cited

U.S. PATENT DOCUMENTS 2,302,707 11/1942 Mejean ........................... 128/202.27
4,157,092 6/1979 Fare et al. .

FOREIGN PATENT DOCUMENTS 749034 8/1944 Fed. Rep. of Germany ........................ 128/202.27

Primary Examiner—Eugene H. Eickholt
Attorney, Agent, or Firm—Walter Ottesen

[57] ABSTRACT

The invention is directed to a pumping arrangement for supplying a ventilating apparatus with breathing gas. The pumping arrangement includes a piston which runs in a cylinder and the piston is connected via a coupling with a drive unit for generating the pumping strokes. The coupling engages a motion transmitter in the form of a piston rod. Gas connecting ports for the breathing gas to be pumped open into the inner chamber of the cylinder. The pumping arrangement permits the piston-cylinder unit to be simply removed and to be reinstalled with reliable guidance. An automatic latching occurs such that a release and removal of the piston-cylinder unit from the ventilating apparatus and its uncoupling from the drive unit is possible only in a rest condition and not during operation. For exchanging the piston-cylinder unit, the motion actuator in the form of the piston rod moves through a preparatory stroke having an end position in which the coupling as well as the latching of the piston-cylinder unit with respect to the housing can be actuated.

11 Claims, 3 Drawing Sheets

PUMPING ARRANGEMENT FOR SUPPLYING A VENTILATING APPARATUS WITH BREATHING GAS

FIELD OF THE INVENTION

The invention relates to a pumping arrangement for supplying a ventilating apparatus with breathing gas. The pumping arrangement includes a piston which moves in a cylinder. A coupling is provided which engages a moving drive and the piston is connected to a drive unit via this coupling for generating the pumping strokes.

BACKGROUND OF THE INVENTION

A pumping arrangement of this kind is disclosed in U.S. Pat. No. 4,157,092. This pumping arrangement pumps breathing gas into the breathing circuit of a ventilating apparatus. The pumping arrangement includes a piston-cylinder unit which is insertable into the housing of the ventilating apparatus and can again be removed therefrom. The base plate of the piston carries annular inserts of ferromagnetic material which serve as a coupling aid and which are contacted and rigidly held by permanent magnets. These magnets are accommodated in a disc which is attached to a motion actuator which is configured as a displacement rod connected to a drive unit. The magnets take the piston along during the pumping strokes and thereby transmit the pump strokes for the breathing gas. Connecting lines are fixedly connected to the piston-cylinder unit for leading the breathing gas into and out of the pumping arrangement.

In the known pumping arrangement, the piston-cylinder unit can be removed during the operation of the drive unit or it can self-loosen whereby unwanted operational disturbances can occur. For removal, additional manipulation is required for loosening the gas lines. The piston is not fixed when the piston-cylinder unit is removed. Uncontrolled displacements occurring during manipulation can lead to damage or prevent a later coupling.

SUMMARY OF THE INVENTION

It is an object of the invention to provide a pumping arrangement of the kind described above which is improved so that the piston-cylinder unit is simple to remove and can be reliably reinstalled. It is a further object of the invention to provide a pumping arrangement wherein an automatic latching occurs in such a manner that a release and removal of the piston-cylinder unit from the ventilating apparatus and its uncoupling from the drive unit is only possible in a rest condition and not during operation.

The pumping arrangement of the invention is for supplying a ventilating apparatus with breathing gas. The pumping arrangement includes: a housing; a piston-cylinder unit removably mounted in the housing, the piston-cylinder unit including a cylinder and a piston mounted in the cylinder so as to perform a reciprocating movement having a predetermined stroke length; the cylinder and the piston conjointly defining a work chamber in which the breathing gas is pumped; gas line connection means for conducting the breathing gas to and away from the work chamber; a drive unit mounted in the housing for generating the reciprocating movement for the piston; motion transmitting means for transmitting the reciprocating movement of the drive unit to the piston; coupling means for releasably coupling the motion transmitting means to the drive unit; control means for operating on the drive means so as to cause the motion transmitting means to pass through a preparatory stroke having an end position; latching means for releasably latching the piston-cylinder unit with respect to the housing; and, actuating means for actuating the latching means and the coupling means when the motion transmitting means is in the end position to permit removal or installation of the piston-cylinder unit.

According to a feature of the invention, the motion transmitter performs a preparatory stroke having an end position in which the coupling as well as a latching of the piston-cylinder unit with respect to the housing are actuable for exchanging the piston-cylinder unit. A removal of the piston-cylinder unit can only then take place when the pumping arrangement is deliberately switched into a preparatory position in which the stroke movement of the motion transmitter brings the latter into an end position. In this end position, the piston is fixed with respect to the cylinder. A removal and a subsequent reinstallation of the piston-cylinder unit therefore makes possible a reliable uncoupling and coupling of the motion transmitter with the drive unit so that an adjustment of the position of the motion transmitter in advance of the reinstallation is not required. By generating the preparatory stroke and the restraint of the motion transmitter in the end position, the position of the drive unit and the coupling corresponding thereto is fixed until the drive unit is again actuated for carrying out pumping strokes after installation of the piston-cylinder unit.

The control of the stroke movements is preferably registered by means of a displacement sensor and transmitted to the control unit so that with the drive unit switched on, the limits of the pumping strokes are determined by means of the displacement sensor. When switching off the drive unit, the control over the displacement sensor is then lifted and the motion transmitter is brought into its preparatory position by means of a longer preparatory stroke.

An especially reliable and resistance-free sliding of the piston in the cylinder is made possible by means of a double-roll membrane.

Preferably, the piston is locked in its position and the motion transmitter placed at rest with the aid of the detent means when actuating the actuating means for uncoupling the motion transmitter via the coupling means and removing the piston-cylinder unit. Damage, for example, to the sealing surfaces by means of a piston which would otherwise be freely movable is prevented. In this way, the position of the piston relative to the cylinder, which it assumes when removing the piston-cylinder unit, also remains fixed during a follow-on maintenance operation, cleaning, disinfection or other manipulation. Thereafter, the piston can be again coupled in the same position after the above-mentioned work has been carried out. Furthermore, when exchanging different piston-cylinder units in the housing of the pumping arrangement, it is assured that the same position applies for all units for a quick and reliable reinstallation.

The openings of the gas connecting lines are connectable via sealing elements to their gas supply lines simultaneously with the actuation of the actuating means. In this way, the pumping arrangement is operationally ready for pumping the breathing gas directly after installation of the piston-cylinder unit.

In the pumping arrangement according to the invention, a motion transmitter in the form of a piston rod is provided. A coupling unit is connected with the piston rod to provide a form-tight coupling of the latter to the drive unit. The piston rod has a head-shaped end and the coupling unit includes at least two pivot jaws which engage behind the head-shaped end of the piston rod. The pivot jaws are resiliently biased in the clamping direction and can be lifted from the head-shaped end by means of pressure pins. For this purpose, a cam plate attached to a coupling piece of the coupling unit is rotated and is provided with an inclined camming surface for engaging the engaging surfaces of the pins. The camming surface acts against the pulling force of the resiliently biased pressure pins. The form-tight engagement of the pivot jaws behind the head-shaped end assures a rigid connection between the piston rod and the drive unit during the pumping stroke. However, the pivot jaws can release the piston rod in response to jolt-like drive movements to such an extent that the jolt movements are smoothed and are not transmitted to the patient via the breathing gas. The foregoing notwithstanding, the spring force with which the pivot jaws engage behind the head-shaped end of the piston rod is adequate to follow subsequent uniform stroke movements. At the end of the preparatory stroke, the pivot jaws release the head-shaped end of the piston rod as soon as the pressure pins press the pivot jaws away from the head-shaped end by means of the rotational movement of the cam plate.

According to another feature of the invention, a cam disc is mounted on the piston-cylinder unit so as to be actuable via a pivot handle. The cam disc has a switching pin which engages in a drive slot of the cam plate when the piston-cylinder unit is seated in the housing. By pivoting the handle, the connection of the coupling unit and the piston rod as well as the connection of the pneumatic interface locations between the gas connecting ports and their gas supply lines is established. The pivoting of the handle rotates the cam plate so that the inclined cam surface is directed against the engaging surfaces of the pressure pins whereby the pivot jaws are lifted up from the head-shaped end of the piston rod (unlatching). When the handle is pivoted back to its initial position, the inclined cam surface is removed from the engaging surfaces of the pressure pins so that the pivot jaws are again biased by the spring pulling force and engage behind the head end of the piston rod (latching).

According to another feature of the invention, the pivot handle supports a cam disc at its pivot axis and this cam disc is provided with a latching recess. A latching member engages the latching recess and is displaceable from this recess when the end position of the preparatory stroke is reached. During the pumping strokes, the latching member engages the latching recess and prevents an actuation of the pivot handle and thereby prevents an unwanted uncoupling of the piston-cylinder unit from the drive unit during operation. Only in the end position of the preparatory stroke is it possible to remove the latching member from the latching recess and uncouple the piston-cylinder unit.

It is advantageous to configure the latching member as a resilient tongue which engages into the latching recess and to further provide a thickening on the piston rod by means of which the resilient tongue is pressed out of the latching recess when the preparatory stroke is carried out. In this way, an automatic release of the pivot handle is provided for uncoupling the piston-cylinder unit from the drive unit as soon as the preparatory stroke is completed.

A stroke detent device is provided in order to prevent a relative movement of the piston to the cylinder when the piston-cylinder unit has been removed and to simplify a subsequent installation and coupling thereof. For this purpose, a detent recess is provided on the piston rod in which a detent slide engages in the end position of the preparatory stroke when the piston-cylinder unit has been removed. The detent slide is resiliently biased into its detent position and is in engagement with a release pin when the piston-cylinder unit is seated in the housing. The release pin unlatches the stroke detent device so that the working strokes can be carried out during operation.

The end face of the cylinder is an advantageous location for mounting the pivot handle and has a pivot shaft which is displaced radially from the longitudinal axis of the cylinder. The pivot handle is provided with a cam disc on its pivot shaft. When actuating the pivot handle for coupling the motion actuator to the drive unit, the piston-cylinder unit is tipped about a support by means of a wobble movement of the cam disc and the openings of the gas connecting ports lying in the pivot plane at the outer periphery of the cylinder are pressed onto corresponding ones of the gas supply lines. The pivot movement is made possible in that the cam disc is pressed against a pressure piece during actuation of the pivot handle whereby the pivot-cylinder unit performs a pivot movement about the support which acts as a tilt point and the connecting ports are pressed against lip seals. In this way, a leak-free seal of the connecting ports is made possible when the piston-cylinder unit is latched.

A displacement sensor senses the end of the pumping stroke and switches the course of the pumping stroke by means of a control unit. The preparatory stroke can be carried out only after an intended override of the control provided by the displacement sensor, for example, by means of a special switching action at the control unit.

BRIEF DESCRIPTION OF THE DRAWINGS

The invention will now be described with reference to the drawings wherein.

DESCRIPTION OF THE PREFERRED
EMBODIMENTS OF THE INVENTION

Figure 1:
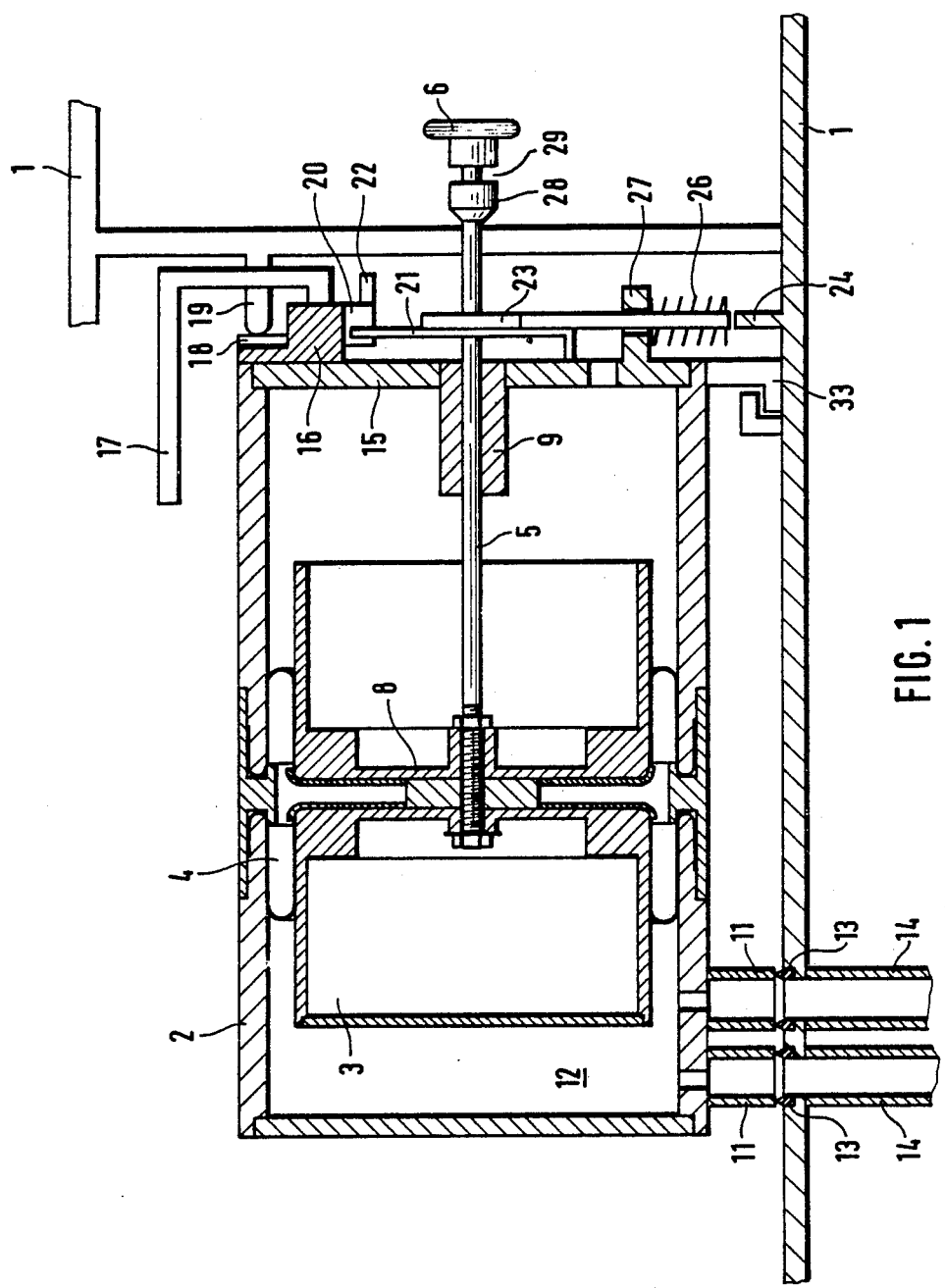
FIG. 1 is a partial view of the pumping arrangement according to the invention wherein the piston-cylinder unit is shown, partially in section, with the piston in its midstroke position.

FIG. 1 shows the piston-cylinder unit, in section, as it is seated on the housing of a ventilating apparatus. The housing 1 is not completely illustrated and only those elements thereof are shown which are needed for the explanation of the invention.

Figure 2:
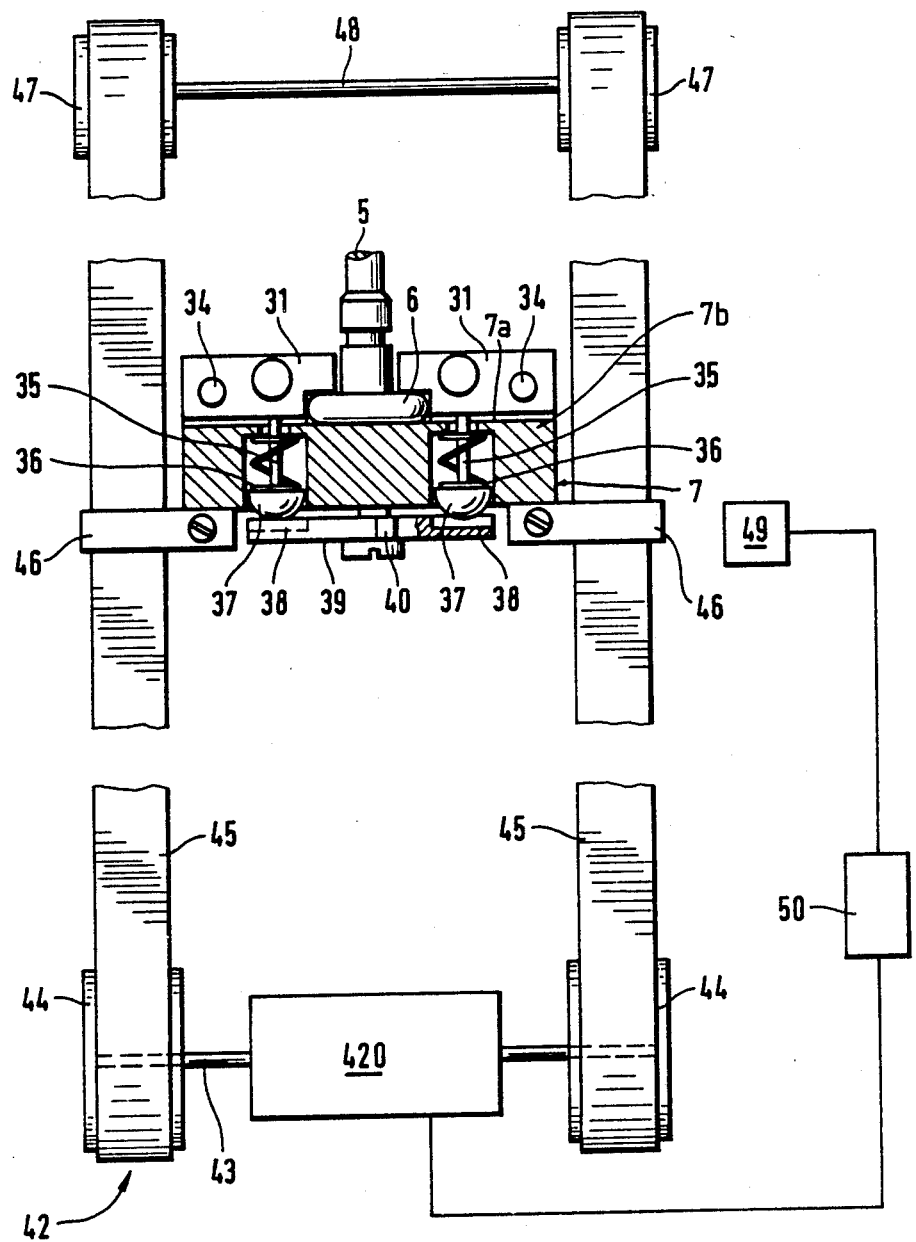
FIG. 2 is a plan view of the coupling unit and the drive unit for the piston rod; and, FIG. 3 is a view of the cam disc having the latching recess and showing the latching member in engagement therewith as well as the stroke detent device.

The main components of the piston-cylinder unit are the cylinder 2 in which a piston 3 is received via a double-roll membrane. The stroke movements of the piston 3 are generated by a drive unit 42 shown in FIG. 2 via a motion transmitter configured as a piston rod 5. The drive unit 42 engages a head-shaped or T-shaped holder 6 of the drive rod 5 by means of a coupling unit 7 which is shown in FIG. 2. The piston rod 5 is attached to an intermediate base 8 of the piston and is displaceably journalled in a sleeve bearing 9.

The piston 3 and the cylinder 2 conjointly define a work chamber 12 provided with gas connecting ports 11. The gas connecting ports 11 are connected with corresponding ones of the supply lines 14 via lip seals 13. The end plate 15 of the cylinder 2 carrying the sleeve bearing 9 has a cam disc 16 from which a pivot handle 17 extends. The cam disc 16 includes on the one hand an inclined cam surface 18 which lies against a pressure piece 19 attached to the housing 1 and, on the other hand, includes a latching recess 20 into which a latching member 21 engages. Furthermore, a switching pin 22 projects outwardly parallel to the axis of rotation of the cam disc 16.

To the rear of the end plate 15, a detent slide 23 is mounted which surrounds the piston rod 5 without making any contact therewith for the pumping stroke position of the piston-cylinder unit (2, 3) shown. A release pin 24 in the housing 1 holds the detent slide 23 in this position when the cylinder 2 is seated in the housing. A retaining spring 26 braces against a holder 27 which is configured so that the detent slide 23 passes therethrough as shown. The latching member 21 likewise surrounds the piston rod 5 without hindering the piston movement. A thickening 28 as well as a detent recess 29 are provided on the piston rod 5 in the immediate vicinity of the holder 6.

During a pumping stroke, the piston rod 5 slides back and forth in the sleeve bearing 9 as well as through the latching member 21 and the detent slide 23 when driven by the drive unit 42 via the coupling unit 7. The stroke movements of the piston 3 are made possible by the rolling movement of the double-roll membrane 4 on the inner surface of the piston 2. The double-roll membrane 4 surrounds the peripheral surface of the piston as shown in FIG. 1.

The pivot handle 17 is blocked with respect to its pivot movement by the latching member 21 latched in the latching recess 20. In this way, a removal of the piston-cylinder unit (2, 3) from the housing 1 is not possible since the pressure piece 19 does not allow any freedom of movement so as to permit the piston-cylinder unit anchored in the hook support 33 to be removed. The pressure piece 19 rests against the inclined cam surface 18 of the cam disc 16. At the same time, the pressure applied against the inclined cam surface 18 of the cam disc 16 effects a tilting movement about the hook support 33 so that the gas connecting ports 11 are braced tightly against the lip seals 13.

The coupling unit 7 is shown in FIG. 2 and includes pivotally-mounted jaws which engage over the holder 6 of the piston rod 5. The pivot jaws 31 are received in pivot joints 34 and are connected to respective pressure pins 35. For the position shown in FIG. 2, the pressure pins 35 are subjected to the pressure force of respective pressure springs 36 and thereby provide a clamping action of the pivot jaws 31 against the holder 6. Each pin head 37 lies opposite an inclined cam surface 38 which is formed in a rotatably mounted cam plate 39. The cam plate 39 is provided with a drive slot 40 in which the switching pin 22 of the cam disc 16 can engage.

The stroke movements are transmitted within a drive unit 42 from a drive motor 420 via its drive shaft 43 to the drive wheels 44 and from there the stroke movements are transmitted via toothed belts 45 to the coupling unit 7. Screw clamps 46 are provided for attaching the coupling unit 7 to the toothed belts 45. The toothed belts 45 run over two running wheels 47 back to the drive wheels 44. The running wheels 47 are mounted on a shaft 48. The position of the pump stroke is monitored by a light-beam curtain 49 which serves as a displacement sensor and transmits a position signal to the control unit 50 by means of which the drive unit is controlled with respect to speed and direction of rotation to provide the reciprocating movement.

Figure 3:
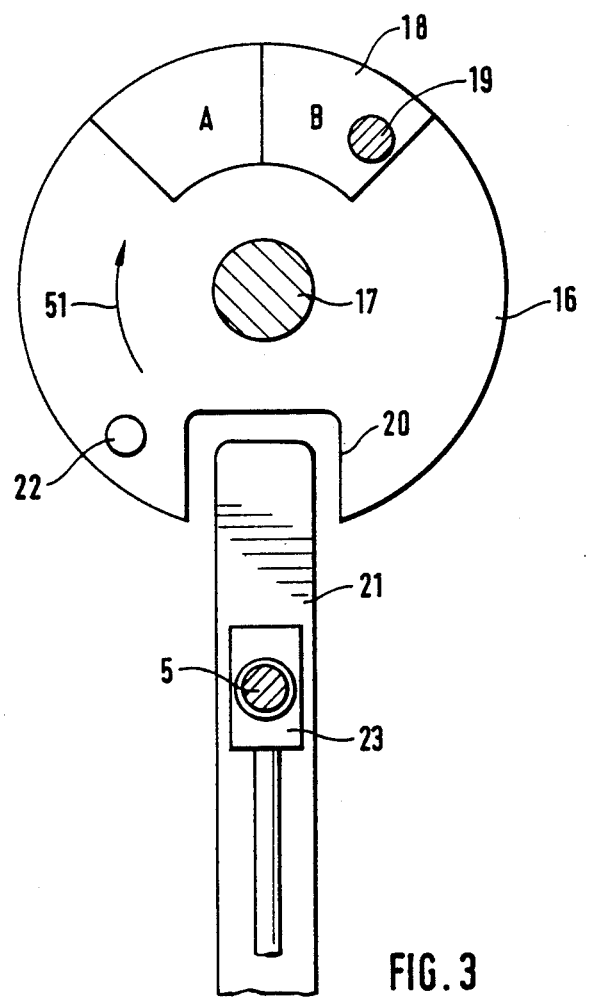

FIG. 3 is a plan view of the cam disc 16 seen looking toward the end plate 15. The cam disc 16 includes a cam surface 18 at its upper periphery which is subdivided into a depressed component surface A and an inclined elevated component surface B. At the lower periphery of the cam disc 16, the latching recess 20 is disposed into which the latching member 21 engages. A switching pin 22 extends outwardly from the cam disc 16.

Also in FIG. 3, the piston rod 5 is shown surrounded by a detent slide 23 in which a bore is provided having a diameter such that the piston rod 5 as well as the thickening 28 pass therethrough. The latching member 21 likewise has a bore through which the piston rod 5 passes but not the thickening 28.

The piston-cylinder unit is uncoupled from the drive unit 32 in the manner described below.

First, the piston rod 5 passes through a preparatory stroke which can, for example, be initiated by an appropriate selection switch on the control unit 50. With this movement, the holder 6 is displaced by the coupling unit 7 so far forward in the direction of the work chamber 12 that the thickening 28 passes through the detent slide 23 and comes against the latching member 21 thereby displacing the same out of the latching recess 20. At the same time, the switching pin 22 engages into the drive slot 40. The detent slide 23 remains outside of the detent recess 29.

By pivoting the pivot handle 17, the component surface B of the cam surface 18 lying against the pressure piece 19 is displaced so that now the component surface A spaced from the pressure piece 19 is opposite to the latter while, on the other hand, the cam plate 39 is pivotally rotated by means of the switching pin 22 in engagement with the drive slot 40. In this way, the cam plate 39 is rotated from the first end position shown in FIG. 2 to its second end position so that its inclined cam surfaces 38 run up against the pin heads 37. The pressure pins 35 are moved against the spring force of the pressure springs 36 so that the pivot jaws 31 release the holder 6.

The piston-cylinder unit (2, 3) can now be taken out of the housing 1 by means of the pivot handle 17. With this step, the detent slide 23 is removed from the release pin 24 so that the detent spring 26 pulls the detent slide 23 into the detent recess 29. This fixes the position of the piston rod 5.

The holder 6 is placed between the opened pivot jaws 31 when the piston-cylinder unit (2, 3) is again seated in the housing and latched as well as coupled to the drive unit 42. At the same time, the following occurs: the switching pin 22 engages into the drive slot 40, the detent slide 23 is lifted by the release pin 24 and is disengaged from the detent recess 29 so that the piston rod 5 is released. At the same time, the cam disc 16 is brought into its blocking position in which the component surface B of the cam surface 18 is rotated against the pressure piece 19 thereby tipping the entire piston-cylinder unit about the hook support 33 and pressing the gas connecting ports 11 against their lip seals 13. Simultaneously with the rotational movement of the cam disc 16, the switching pin 22 moves the cam plate 39 into its latching position whereby the inclined cam surfaces 38 thereof release the pin heads 37 of the pressure pins 35 so that these pressure pins press the pivot jaws 31 against the holder 6 under the pressure action of their pressure springs 36. In this way, the holder 6 lies against the holding surface 7a of the coupling piece 7b.

In the entire operation of the latching described up to now, the latching member 21 does not yet engage the latching opening 20; instead, this is first effected by means of the first pumping stroke in the direction away from the end plate 15 since only then is the thickening 28 on the piston rod 5 removed from the latching member 21 so that this resilient tongue-shaped member can jump back into the latching recess 20. Now the cam disc 16 is blocked and a release and removal of the piston-cylinder unit (2, 3) during the pumping strokes is no longer possible.

All manipulations for latching, coupling and removal of the piston-cylinder unit (2, 3) are carried out solely by actuating the pivot handle 17. The remaining functions occur as a consequence of the actuation of the pivot handle 17.

It is understood that the foregoing description is that of the preferred embodiments of the invention and that various changes and modifications may be made thereto without departing from the spirit and scope of the invention as defined in the appended claims.

What is claimed is:

1. A pumping arrangement for supplying a ventilating apparatus with breathing gas, the pumping arrangement comprising:
    a housing;
    a piston-cylinder unit removably mounted in said housing, said piston-cylinder unit including a cylinder and a piston mounted in said cylinder so as to perform a reciprocating movement having a predetermined stroke length; said cylinder and said piston conjointly defining a work chamber in which the breathing gas is pumped;
    gas line connection means for conducting the breathing gas to and away from said work chamber;
    a drive unit mounted in said housing for generating the reciprocating movement for said piston;
    motion transmitting means for transmitting the reciprocating movement of said drive unit to said piston;
    coupling means for releasably coupling said motion transmitting means to said drive unit;
    control means for operating on said drive means so as to cause said motion transmitting means to pass through a preparatory stroke having an end position;
    latching means for releasably latching said piston-cylinder unit with respect to said housing; and,
    actuating means for actuating said latching means and said coupling means when said motion transmitting means is in said end position to permit removal or installation of said piston-cylinder unit.

2. The pumping arrangement of claim 1, said piston-cylinder unit including a double-roll membrane for sealing said piston with respect to said cylinder.

3. The pumping arrangement of claim 1, comprising stroke detent means for fixing said piston in a predetermined position relative to said cylinder when said actuating means actuates said latching means and said coupling means.

4. The pumping arrangement of claim 1, comprising: gas line supply means for conducting the breathing gas into and away from said gas line connection means; said gas line supply means and said gas line connection means conjointly defining a gas line interface at which said gas line connection means is separated from said gas line supply means when said piston-cylinder unit is removed from said housing; and, sealing means disposed at said gas line interface; and, said actuating means including means for applying a force to said cylinder for connecting said gas line connection means to said gas line supply means via said sealing means.

5. The pumping arrangement of claim 1, said motion transmitting means being a connecting rod having a first end connected to said piston and a second end defining a T-shaped holder; said coupling means comprising a mounting member connected to said drive unit; two pivot jaws pivotally mounted on said mounting member for pivotally moving between a holding position whereat said jaws hold said connecting rod at said holder against said mounting member and a release position whereat said holder can be uncoupled from said coupling means; two pressure pins connected to said jaws, respectively, for actuating the latter; resilient means interposed between said pins and said mounting member for resiliently biasing said jaws into said holding position; and, cam means defining a cam surface and being rotatably mounted on said mounting member; and, connecting means for operatively connecting said actuating means to said cam means for rotating the latter between a first position whereat said jaws are in said holding position and a second position whereat said cam surface acts on said pins and against the force of said resilient means to bring said jaws into said release position.

6. The pumping arrangement of claim 5, said actuating means including: a pivot handle pivotally mounted on said cylinder; and, a cam disc mounted on said pivot handle so as to rotate between a lock position and an unlock position when said pivot handle is pivotally moved; and, said connecting means including: drive slot means formed in said cam means; and, a switching pin mounted on said cam disc and engaging said drive slot means for rotating said cam means between said first and second positions thereof when said cam disc is rotated between said lock and unlock positions.

7. The pumping arrangement of claim 6, said latching means including: a latching recess formed in said cam disc; and, a displaceable latching member for engaging said latching recess to hold said cam disc in said lock position; and, said actuating means including displacing means mounted on said connecting rod for displacing said latching member from said latching recess when said connecting rod reaches said end position of said preparatory stroke.

8. The pumping arrangement of claim 7, said latching member being a resilient tongue-like member having a pass-through opening of predetermined width formed therein for accommodating the movement of said connecting rod therein; and, said displacing means being a thickening formed on said connecting rod and having a width greater than said predetermined width of said pass-through opening so as to permit said thickening to strike and displace said tongue-like latching member out of said latching recess when said connecting rod reaches said end position thereby enabling said cam disc to be rotated out of said lock position via said pivot handle.

9. The pumping arrangement of claim 6, said pumping arrangement further comprising: gas line supply means for conducting the breathing gas into and away from said gas line connection means; said gas line supply means and said gas line connection means conjointly defining a gas line interface at which said gas line connection means is separated from said gas line supply means when said piston-cylinder unit is removed from said housing; sealing means disposed at said gas line interface; said gas line connection means being mounted on said cylinder so as to communicate with said work chamber; and, a tilt support mounted on said housing about which said piston-cylinder unit is tilted into a seated position when the same is installed in said housing; and, said actuating means including a stationary cam follower mounted on said housing; said cam disc including a cam surface for coacting with said cam follower when said pivot handle is pivoted to rotate said cam disc from said unlock position to said lock position thereby imparting a tilting movement to said piston-cylinder unit so as to tilt the latter about said tilt support into its seated position while at the same time pressing said gas line connection means against said sealing means for connecting said gas line connection means to said gas line supply means via said sealing means.

10. The pumping arrangement of claim 1, comprising stroke detent means for fixing said connecting rod in said end position after said actuating means has actuated said latching means and said coupling means and when said piston-cylinder unit is removed from said housing; and, said detent means including: detent recess means formed on said connecting rod; a detent slide slideably mounted on said cylinder for movement between a release position and a connecting rod detent position at which said detent slide engages said detent recess means for fixing said connecting rod in said end position thereof; a release pin mounted on said housing for holding said detent slide in said release position so long as said piston-cylinder unit is seated in said housing; and, resilient means for resiliently biasing said detent slide into said detent position whereby said detent slide slides into said detent position when said piston-cylinder unit is removed from said housing; and, said release pin being mounted in said housing so as to contact engage said detent slide when the piston-cylinder unit is installed in said housing so as to cause said detent slide to be pushed against the force of said resilient means back into said release position.

11. The pumping arrangement of claim 1, said control means including a displacement sensor for controlling the reciprocating movement of said piston through said predetermined stroke length.

* * * * *